United States Patent [19]

Cavazza

[11] 4,343,816

[45] Aug. 10, 1982

[54] PHARMACEUTICAL COMPOSITION COMPRISING AN ACYL-CARNITINE, FOR TREATING PERIPHERAL VASCULAR DISEASES

[76] Inventor: Claudio Cavazza, 35, Via Marocco, 00144 Rome, Italy

[21] Appl. No.: 118,835

[22] Filed: Feb. 5, 1980

[30] Foreign Application Priority Data

Feb. 12, 1979 [IT] Italy .............................. 47976 A/79

[51] Int. Cl.³ ........................................... A61K 31/205
[52] U.S. Cl. ................................................. 424/316
[58] Field of Search ......................................... 424/316

[56] References Cited

U.S. PATENT DOCUMENTS 3,793,450  2/1974  Schnell ................................ 424/343
3,810,994  5/1974  Wiegard .............................. 424/316

Primary Examiner—Stanley J. Friedman
Attorney, Agent, or Firm—Ladas & Parry

[57] ABSTRACT

A pharmaceutical, acyl carnitine-containing composition wherein the acyl radical is selected from the group comprising acetyl, propionyl, butyryl, hydroxybutyryl and acetoacetyl is disclosed. This composition is useful in the therapeutic treatment of peripheral vascular diseases (typically, Raynaud's disease).

6 Claims, 24 Drawing Figures

PHARMACEUTICAL COMPOSITION COMPRISING AN ACYL-CARNITINE, FOR TREATING PERIPHERAL VASCULAR DISEASES

The present invention relates to a pharmaceutical composition and a therapeutical method for the treatment of peripheral vascular diseases.

More specifically, the present invention relates to a pharmaceutical composition and a therapeutical method for the treatment of:

(1) Chronic arterial occlusions of the limbs, meaning by this term a heterogenous group of diseases with a chronic course the development of which brings about progressive narrowing and even total occlusion of the involved arteries and consequent, inevitable tissue ischaemia (typically: atherosclerosis);

(2) Functional arterial diseases, meaning by this term a group of diseases characterized by the presence of more or less widespread disturbances of cutaneous and subctutaneous blood circulation, determined by spasm of small arteries and arterioles (typically: Raynaud's disease); and (3) Ischaemias.

Although hereinafter, for the sake of simplicity, specific reference will be made to atherosclerosis and Raynaud's disease, it must be understood that the therapeutical method of the present invention is applicable to the treatment of every disease nosologically classifiable as chronic arterial occlusion or functional arterial disease.

As is known, atherosclerosis is a degenerative disease of the arteries (of large and medium calibre) the characteristic lesion whereof is the atheromatous plaque. Frequent complications are ulceration of the plaque, subintimal haemorrhages and thrombus formation on the ulcerated area with possible detachment of the emboli. Progressive narrowing, until occlusion occurs, of the vasal lumen is the final result of the atheromatous plaque formation.

As far as the extremites are concerned, the more frequently involved arteries are those of the lower extremities. The patient displays ischaemic symptomatology characterized by pain and trophic disturbances. In the more severe cases necrosis of even extended parts of the extremities (grangrene) may occur.

Rayaud's disease is characterized by intermittent spasm of the digit arteries, generally brought on by cold.

The paroxysmal crises typical of Raynaud's disease present three characteristic stages: cutaneous pallor (due to reduced blood flow in the capillaries); cyanosis (due to overloaded and dilated capillaries caused by stagnation); cutaneous reddening (due to hyperaemia accompanied by violent pain).

There are a multiplicity of therapeutic means, both pharmacological and surgical, used hitherto for the treatment of the aforementioned pathological conditions.

Drugs acting upon the lipid metabolism have been in use for some time in atherosclerosis (cholestyramine, methyl-neomycine, nicotinic acid, clofibrate, d-thyroxine, estrogens, haparin, dehydrocholate sodium, etc.); fibrinolytic drugs (nicotinic acid and clofibrate); anticoagulants (haparin, dicumarol) and vasoactive agents (papaverine).

All such drugs present inconveniences, sometimes so severe that the use of some of them has recently been discouraged.

Although many such drugs prove to be useful for the prevention of the disease, they are poorly or not efficacious at all when the disease has reached the clinical stage. Others are intolerably toxic, particularly in the case of long term treatment, and in addition they exhibit undesirable side effects.

For instance, the side effects observed in regard to clofibrate include nausea, gastrointestinal disturbances, frequently associated with diarrhoea, sluggishness, headache and dizziness. In addition increased body weight, myalgia, pruritus, examthemas, alopecia and leucopenia have been observed.

Others are dangerous to use, for instance the anticoagulants such as dicumarol the complete toxic effect whereof takes some time to develop. Furthermore, even when the prothrombin is within the optimal range, haemorrhage may occur days or even weeks after administration of the drug has been interrupted.

The use of vasoactive (vasodilators) agents do give rise to no lesser perplexities in the presence of ischaemic disorders, since there appears to exist the danger that the vasodilation which inevitably occurs in non-ischaemic areas produces harmful phenomena diverting blood flow to areas where blood flow is already sufficiently adequate, with aggravation of ischaemia in the tissue area adjacent to the occluded artery.

Surgical therapy involves removing arterial obstruction, operations for replacing an arterial segment with a natural or artificial prosthesis and prosthesis grafts to by-pass the stenotic segment of the artery.

Such surgical operations, however, give rise to perplexities due to the facility whereby the prostheses become occluded, while chemical research has still been not able to make available synthetic materials of proven antithrombogenicity for the production of prostheses.

The traditionally employed drugs for treating Raynaud's disease are peripheral vasodilators, ganglioplegics and depressants of the vasopressure centres. Reserpine and alpha-methyldopa are among the most widely used drugs, but are poorly effective in prolonged treatment. In addition, alpha-methyldopa presents considerable untoward side effects such as sluggishness, psychic depression, gastrointestinal disturbances and diarrhoea.

Surgical therapy mainly comprises dorsal sympathectomy which is generally regarded as an eccessively demolishing operation in comparison with the extent of the disease. Furthermore, such an operation has occasionally shown to be unresolving, since some patients have complained of crises even after sympathectomy.

In view of the foregoing known pharmacological and surgical therapies for the treatment of the aforementioned peripheral vascular diseases, a need is felt for a method of treatment enabling better therapeutic results than those obtained hitherto, without resorting to surgical operations whatever their nature and without employing drugs which give rise to undesiderable side effects.

Therefore, the object of the present invention is to provide a method of treatment for peripheral vascular diseases and the therapeutical agents and the pharmaceutical compositions for such a method.

In accordance with the present invention, a pharmaceutical composition for the treatment of peripheral vascular diseases comprises an amount effective for inducing an anti-ischaemic effect of an acyl-derivative of carnitine represented by the general formula (1)

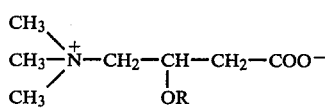

where R is an acyl radical of a fatty acid having 2 to 20 carbon atoms or a pharmacologically acceptable salt, ester or amide thereof and a pharmacologically acceptable excipient therefor.

Also in accordance with the present invention, the therapeutical method for the treatment of peripheral vascular diseases comprises administering to patients affected by chronic arterial occlusions of the extremities, functional arterial diseases and ischaemias an effective amount so as to achieve in such patients and anti-ischaemic effect of an acyl-derivative of carnitine represented by the general formula (1)

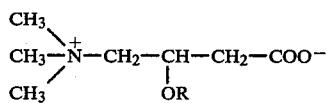

where R is an acyl radical of a fatty acid having 2 to 20 carbon atoms or a pharmacologically acceptable salt, ester or amide therof.

Preferably, the acyl radical R is chosen in the group comprising acetyl, propionyl, butyryl, hydroxybutyryl and acetoacetyl.

The acyl derivative of carnitine of formula (1) or the pharmacologically salts, esters and amides thereof are administered either via the oral route or via the parenteral route.

The dose to be administered will be determined by the attending physician taking the age, weight and general conditions of the patient into account, in accordance with an appropriate professional assessment. Although effective results may be noted at doses as low as 5–8 mg/kg of body weight per day, a dose between approximately 10 and 50 mg/kg of body weight is preferred. Should it be deemed necessary, larger doses can be administered, in view of the remarkably low toxicity of carnitine and the derivatives thereof of formula (1).

As is known, carnitine contains an asymetrical carbon atom and consequently exists in two stereoisomer forms. In the therapeutical method of the present invention the racemic mixture or the isolated optical isomers may be conveniently used, although the L isomer proves to be the more active, while the D isomer is slightly more toxic. The tolerance of acetyl-carnitine and the acyl-derivatives of carnitine of formula (1), either in the racemic mixture form or in the separated optically active forms, is excellent whatever the route of administration. The following Table A shows the LD$_{50}$ as an example in the mouse via the intravenous route, as assessed for varied acyl-derivatives by the Litchfield and Wilcoxon method (Litchfield, J. T., and Wilcoxon F., J. Pharm. Exptl. Therap. 96, 99, 1949).

TABLE A

| | LD$_{50}$ mg/kg via the intravenous route in the mouse |
|---|---|
| acetyl-carnitine | 770 |
| propionyl-carnitine | 761 |

TABLE A-continued

| | LD$_{50}$ mg/kg via the intravenous route in the mouse |
|---|---|
| butyryl-carnitine | 742 |
| hydroxybutyryl-carnitine | 745 |
| hexanoyl-carnitine | 695 |
| octanoyl-carnitine | 630 |
| acetoacetyl-carnitine | 728 |
| succinyl-carnitine | 780 |
| isovaleryl-carnitine | 743 |

In practice, acyl-carnitine (in the racemic form or in the separated stereoisomer forms) is administered either orally or parenterally, in any of the usual pharmaceutical forms prepared by means of conventional processes well known to those skilled in the art. These forms comprise forms of oral unit dosages, either solids or liquids, such as lozenges, capsules, solutions, syrups and the like, and injectable forms such as sterile solutions for ampoules and vials.

Some non-limitative examples of suitable compositions for oral and parenteral administration are given below.

EXAMPLE 1

Solution or sterile aqueous solution containing acetyl-carnitine (in the racemic form or stereoisomer form) or the derivatives thereof in concentrations from 50 mg to 500 mg per ml.

(a) The excipient for injectable ampoules/vials is prepared in accordance with the following non-limitative composition:

| | |
|---|---|
| sodium carboxymethyl cellulose (low viscosity) | 10 mg/ml |
| polysorbate 80 | 4 mg/ml |
| propylparaben | 0.4 ml/ml |
| sufficient water for injections for 1-ml, 2-ml, 5-ml and 10-ml ampoules/vials. | |

(b) The excipient for drip bottles containing 50 ml, 100 ml, 250 ml, 500 ml or 1000 ml, is prepared in accordance with the following non-limitative composition:

| NaCl | 8.6 g/lt |
|---|---|
| KCl | 0.3 g/lt |
| CaCl$_2$ | 0.33 g/lt |
| sufficient water for injections to produce 1 liter. | |

(c) The excipient for bottles for oral administration containing from 5 ml to 100 ml is prepared in accordance with the following non-limitative composition:

| mannitol | 11 mg/ml |
|---|---|
| sorbitol | 600 mg/ml |
| sodium benzoate | 3 mg/ml |
| orange extract | 200 mg/ml |
| vitamin B$_{12}$ | 3 mcg/ml |
| sufficient purified water. | |

EXAMPLE 2

Lozenges containing from 25 mg to 500 mg of acetyl-carnitine (in the racemic mixture form or in the form of separated stereoisomers) or the other acyl-derivatives thereof. The excipient is prepared in accordance with the following non-limitative composition:

| | |
|---|---|
| starch | 45% |
| avicel | 45% |
| talc | 10% |

EXAMPLE 3

Capsules containing from 25 mg to 500 mg of acetyl-carnitine (in the recemic mixture form or in the form of separed stereoisomers) or other acyl-derivatives thereof, without excipients in a non-limitative sense.

The efficacy of the therapeutic method of the present invention has been confirmed by numerous clinical cases, some of which will be later described.

The photoplethysmographic technique, the rheographic technique and the Doppler technique have been used for the clinical study of the patients submitted to the therapeutical method of the present invention.

As is known, photoplethysmography consists in graphic recording by means of a photoelectric cell of changes in transparency to light or in luminescency caused by changes in blood content.

Rheography consists in graphically recording changes in impedance which crosses an extremity segment by means of high frequency sinusoidal electric current. Such changes in impedance are due to changes in the amount of blood contained in the extremity and to the different electric conductivity of blood versus tissue.

The Doppler method consists in the phonic evaluation and graphic recording of the changes in the blood's instantaneous speed, utilizing the Doppler effect.

The aforementioned techniques of investigation are all well known to experts and no further discussion thereof is required.

Clinical cases 2 and 4 (Raynaud's disease and chronic arterial occlusion of the lower extremities respectively) are described with the aid of the attached diagrams wherein:

FIG. 1a and 1b illustrate the photoplethysmographic tracings prior to and following acetyl-carnitine treatment respectively of the second finger of the right hand of clinical case 2;

FIG. 1c and 1d are analogous to FIG. 1a and 1b with respect to the fourth finger of the right hand of clinical case 2;

FIG. 1e and 1f are analogous to FIG. 1a and 1b with respect to the second finger of the left hand of clinical case 2;

FIG. 1g and 1h are analogous to FIG. 1a and 1b with respect to the fourth finger of the left hand of clinical case 2;

Figure 1A:
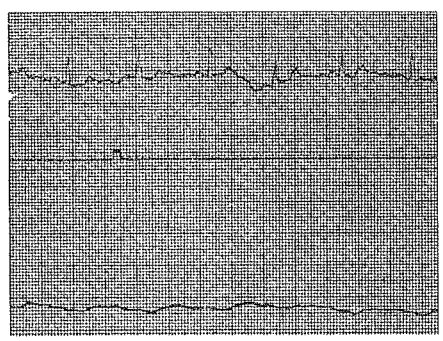
FIG. 1i and 1l are analogous to FIG. 1a and 1b, but with the patient submitted to the cold test.
FIG. 1m and 1n are analogous to FIG. 1c and 1d, but with the patient submitted to the cold test.
FIG. 1o and 1p are analogous to FIG. 1e and 1f, but with the patient submitted to the cold test.
FIG. 1q and 1r are analogous to FIG. 1g and 1h, but with the patient submitted to the cold test.
Figure 1B:
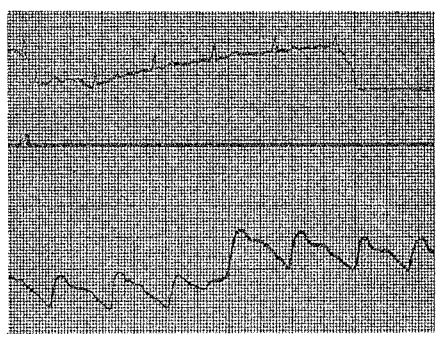
Figure 1C:
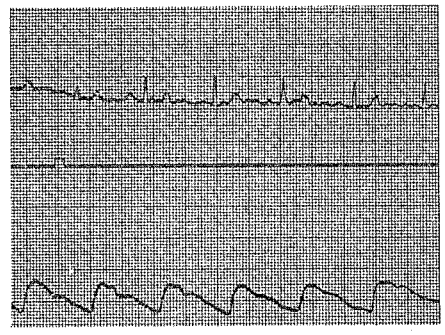
Figure 1D:
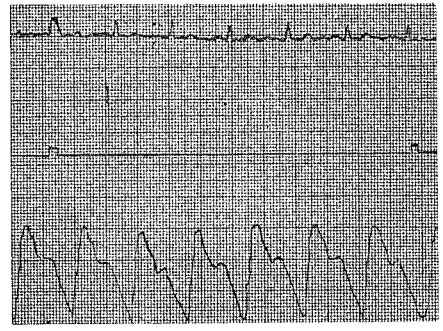
Figure 1E:
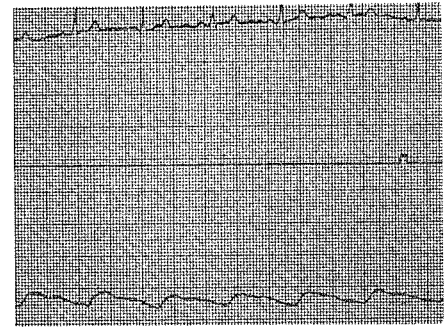
Figure 1F:
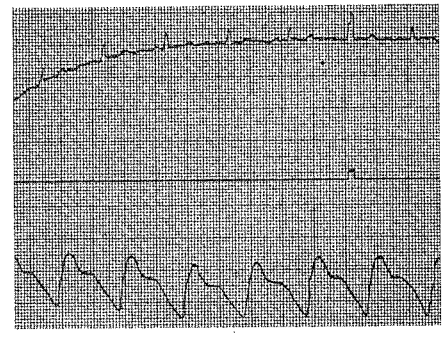
Figure 1G:
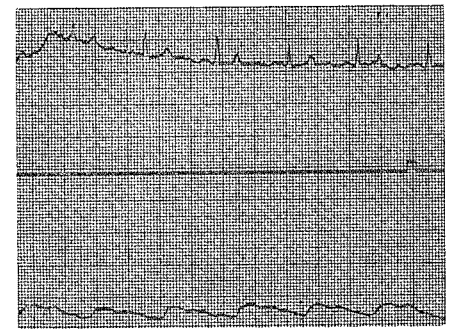
Figure 1H:
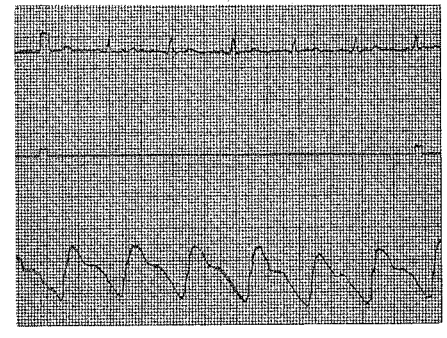
Figure 1I:
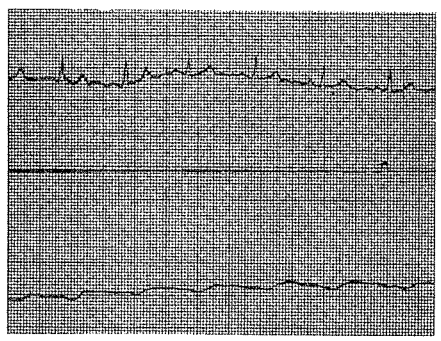
Figure 1L:
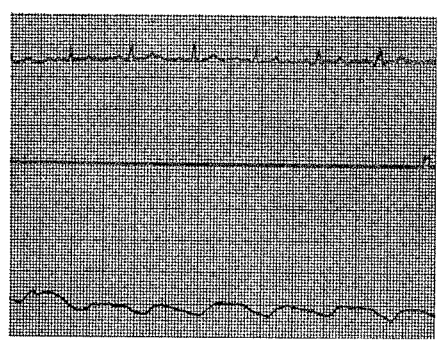
Figure 1M:
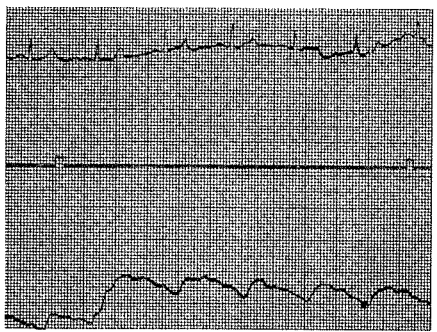
Figure 1N:
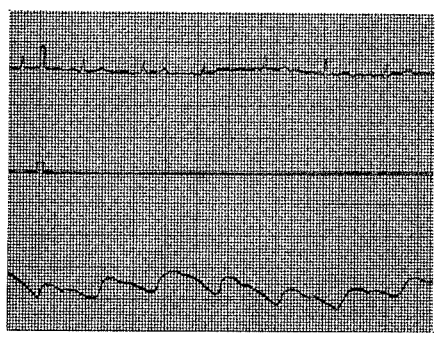
Figure 1O:
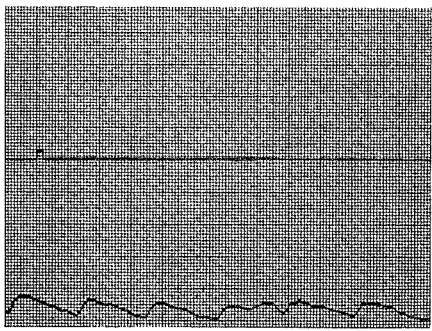
Figure 1P:
Figure 1Q:
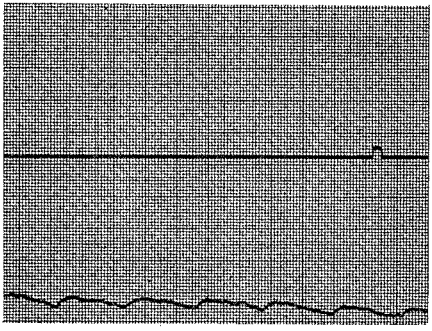
Figure 1R:
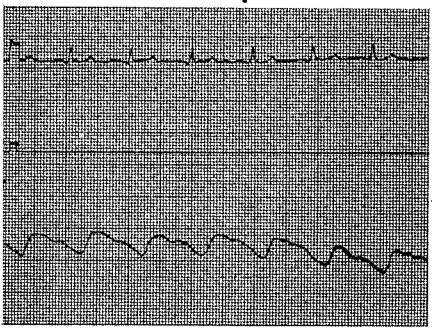
Figure 2A:
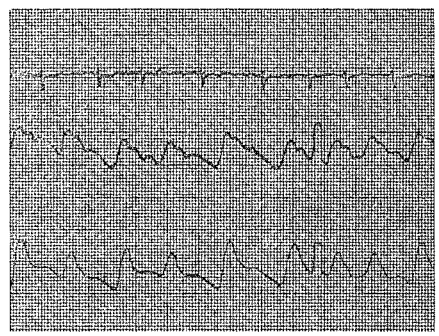
FIG. 2a and 2b illustrate the rheographic and photoplethysmographic tracings, prior to and following acetylcarnitine treatment respectively, of the right leg of clinical case 4.
Figure 2B:
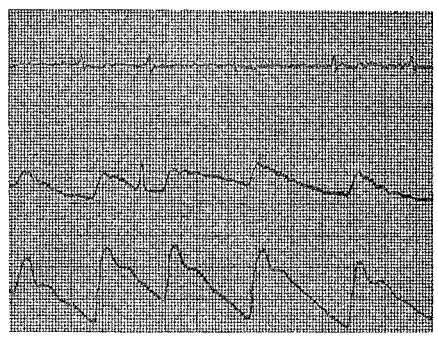
Figure 2C:
Figure 2D:
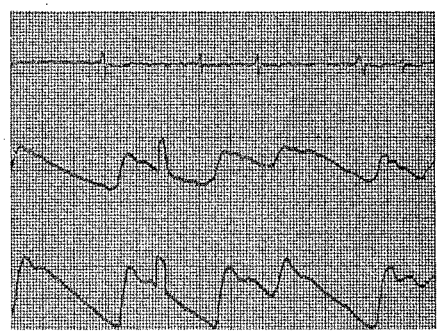
Figure 2E:
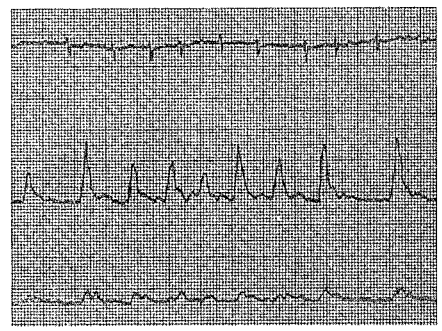
Figure 2F:
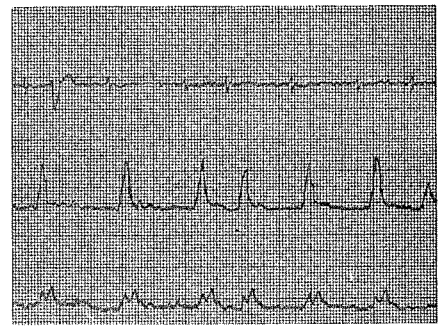
Figure 2G:
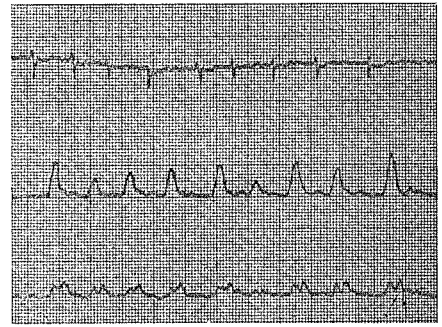
Figure 2H:
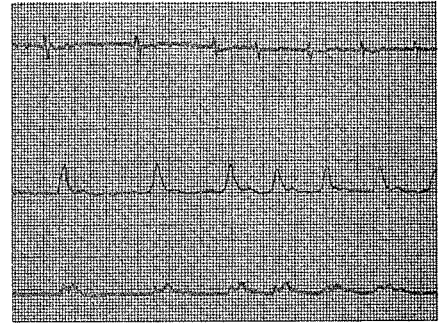

FIG. 2c and 2d are analogous to FIG. 2a and 2b with respect to the left leg of clinical case 4;

FIG. 2e and 2f illustrate the Doppler tracings prior to and following acetyl-carnitine treatment respectively relative to the right posterior tibial artery; and FIG. 2g and 2h are analogous to FIG. 2e and 2f, but relative to the left posterior tibial artery.

In all the Figures, the top tracing is the reference electrocardiogram.

CASE 1

Baseline rheographic and photoplethysmographic tracings of the upper extremities (fingers) were performed in a 53 year old male who exhibited an angiospastic syndrome of the upper extremities. The patient was also submitted to the cold test. The results whereas follows:

- Baseline rheographic tracing: within normal limits
- Baseline photoplethysmographic tracing:
  Markedly reduced sphygmic amplitude with respect to all the fingers;
  Increased crest time with marked enlargement of the ascending branch angle.
  Rounded apex, descending branch with convexity facing the top, dicrotic wave absent.
- Cold test: positive (complete disappearance of the sphygmic wave)

The patient was then administered 4 bottles each of 250 ml of physiological saline containing 500 mg of acetyl-carnitine by phleboclysis for 8 days consecutively.

Upon termination of treatment, rheographic and photoplethysmographic tracing were once again performed as well as the cold test, with the following results:

—Control rheographic tracing: within normal limits
—Control photoplethysmographic tracing: Notably increased sphygmic amplitude versus baseline tracing;
Moderately reduced crest time with notably diminished ascending branch angle;
Apex tending to assume normal morphology. Convexity persists facing the top of the descending branch.
—Cold test: positive (but with the appearance of a slight sphygmic wave)

CASE 2

Baseline photoplethysmographic tracing of the upper extremities was performed in a 31 year old female patient who exhibited an angiospastic syndrome of the upper extremities. She was also submitted to the cold test. The results were as follows (FIG. 1a, 1c, 1e, 1i, 1o, 1q):

- Baseline photoplethysmographic tracing:
  Markedly reduced sphygmic amplitude with respect to all the fingers;
  Increased crest time:
  Moderately rounded apex with attenuated dicrotism.
  Cold test: positive (complete appearance of the sphygmic wave.)

The patient was then administered capsules each containing 500 mg of acetyl-carnitine for four days consecutively, as per the following schedule:

| | |
|---|---|
| 8 a.m.: | 1 capsule |
| 1 p.m.: | 1 capsule |

| | |
|---|---|
| 8 p.m.: | 2 capsules |

Upon termination of treatment, the photoplethysmographic tracing was once again performed as well as the cold test, with the following results
(FIG. 1b, 1d, 1f, 1h, 1n, 1p, 1r):
Control photoplethysmographic tracing: completely normal.
—Col test: negative

CASE 3

Baseline photoplethysmorgraphic tracing of the upper extremities was performed in a 30-year old female patient who exhibited an angiospastic syndrome of the extremities. She was also submitted to the cold test. The results were as follows:

- Baseline photoplethysmographic tracing:
  Markedly reduced sphygmic amplitude with respect to all the fingers;
  Increased crest time;
  Rounded apex, convexity facing the top of the descending branch, dicrotic wave absent.
  Cold test: positive (complete disappearance of the sphygmic wave).

The patient was then administered capsules each containing 500 mg of acetylcarnitine, as per the following schedule.

| | |
|---|---|
| 8 a.m.: | 1 capsule |
| 1 p.m.: | 1 capsule |
| 8 p.m.: | 2 capsules |

Upon termination of treatment, the photoplethysmographic tracing was once again performed as well as the cold test, with the following results:
—Control photoplethysmographic tracing:
Markedly increased sphygmic amplitude;
Increased crest time and the tendency of the apex and the descending branch to take on normal morphology, dicrotic wave attenuated but present.
—Cold test: negative (but with the appearance of a slight sphygmic wave).

CASE 4

Baseline rheographic and photoplethysmographic tracings were performed in a 63-year old patient affected by chronic arterial occlusion, with the following results (FIG. 2a, 2c, 2e, 2g):
—Baseline rheographic tracing
Moderately reduced amplitude;
Increased crest time, descending branch with increased dicrotic incisura time;
increased sphygmic celerity.
—Baseline photoplethysmographic tracing:
Moderately reduced amplitude;
Increased crest time, rounded apex, tendency toward convexity of the descending branch. Increased sphygmic celerity.

The patient was then administered 5 bottles each of 250 ml of physiological saline containing 500 mg of acetyl-carnitine by slow phleboclysis for 20 days consecutively.
Upon termination of treatment, rheographic and photoplethysmographic tracings were once again performed, with the following results:

| (FIG. 2b, 2d, 2f, 2h): | |
|---|---|
| - Rheographic tracing: | considerably improved amplitude and wave morphology |
| - Photoplethysmographic tracing: completely normalized pattern. | |

What is claimed is:
1. Therapeutical method for the treatment of peripheral vascular diseases characterized by the fact of administering to a patient affected by chronic arterial occlusions of the extremities, functional arterial diseases and ischaemias an effective amount as to achieve in said patient an anti-ischaemic effect of an acyl-derivative of carnitine representable by the formula

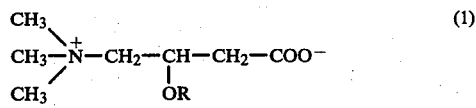

(1)

where R is an acyl radical of fatty acid having 2 to 20 carbon atoms, or a pharmacologically acceptable salt thereof.

2. The therapeutical method according to claim 1, characterized by the fact that said acyl radical R is selected from the group consisting of acetyl, propionyl, butyryl, hydroxybutyryl and acetoacetyl.

3. The therapeutical method according to claim 1, wherein said acyl derivative of carnitine of formula (1) or the pharmacologically acceptable salts thereof is administered via the oral route.

4. The therapeutical method of claim 1, wherein said acyl derivative of carnitine of formula (1) or the pharmacologically acceptable salts thereof is administered via the parenteral route.

5. The therapeutical method of claim 1, wherein the administered amount of said acyl derivative of carnitine of formula (1) or the pharmacologically acceptable salts thereof, is from approximately 10 to approximately 50 mg/kg per day.

6. A pharmaceutical composition for the treatment of peripheral vascular diseases, which comprises an amount effective for inducing an anti-ischaemic effect of an acyl derivative of carnitine represented by the formula

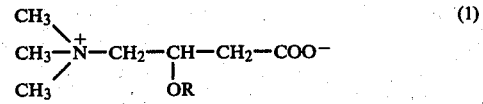

(1)

wherein R is succinyl or isovaleryl, or a pharmacologically acceptable salt thereof, and a pharmacologically acceptable excipient therefor.

* * * * *